US008617582B2

(12) United States Patent
Nouvel

(10) Patent No.: US 8,617,582 B2
(45) Date of Patent: *Dec. 31, 2013

(54) SPOT-ON PESTICIDE COMPOSITION

(75) Inventor: Larry Nouvel, Plano, TX (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/253,690

(22) Filed: Oct. 5, 2011

(65) Prior Publication Data

US 2012/0029033 A1  Feb. 2, 2012

Related U.S. Application Data

(62) Division of application No. 12/888,136, filed on Sep. 22, 2010.

(60) Provisional application No. 61/297,154, filed on Jan. 21, 2010, provisional application No. 61/244,788, filed on Sep. 22, 2009.

(51) Int. Cl.
| | |
|---|---|
| *A01N 25/32* | (2006.01) |
| *A01N 25/02* | (2006.01) |
| *A01N 43/56* | (2006.01) |
| *A01N 37/34* | (2006.01) |
| *A61K 31/4155* | (2006.01) |
| *A61K 31/275* | (2006.01) |
| *A61P 7/04* | (2006.01) |

(52) U.S. Cl.
USPC ............................ 424/405; 514/407; 514/520

(58) Field of Classification Search
USPC ................................. 514/407, 520; 424/405
See application file for complete search history.

(56) References Cited

U.S. PATENT DOCUMENTS

| 4,607,050 A | * | 8/1986 | Kieran et al. | ................. 514/520 |
|---|---|---|---|---|
| 4,737,520 A | | 4/1988 | Naik et al. | |
| 5,602,107 A | | 2/1997 | Choi | |
| 2002/0082294 A1 | | 6/2002 | Sembo et al. | |
| 2008/0031902 A1 | | 2/2008 | Lee et al. | |
| 2008/0038304 A1 | | 2/2008 | Nouvel | |
| 2008/0118585 A1 | | 5/2008 | Nouvel | |
| 2010/0016398 A1 | * | 1/2010 | Sirinyan et al. | ................ 514/407 |
| 2011/0086890 A1 | | 4/2011 | Kelley | |

FOREIGN PATENT DOCUMENTS

| WO | WO 2008/080542 | * | 7/2008 | ............. A01N 53/00 |
|---|---|---|---|---|

OTHER PUBLICATIONS

EPA Office of Pesticide Programs Memorandum ("Pyrethroids: Evaluation of Data from Developmental Neurotoxicity Studies and Consideration of Comparison Sensitivity" Jan. 20, 2010, p. 1-36).*
Miyamoto et al. ("Pyrethroids, nerve poisons: how their risks to human health should be assessed" Toxicology Letters, 1995, 82/83, 933-940).*
Soderlund et al. ("Neurotoxic Actions of Pyrethroid Insecticides" Ann. Rev. Entomol. 34, 1989, 77-96).*
Opinion on Diethylene Glycol Monoethyl Ether (DEGEE) by the Scientific Committee on consumer products (adopted Dec. 19, 2006 and copyrighted 2007 by the European Commission, p. 1-27).
Anadon et al; Use and abuse of pyrethrins and synthetic pyrethroids in veterinary medicine; The Veterinary Journal; 2009; 182:7-20.
Linnett; Permethrin toxicosis in cats; Australian Veterinay Journal; Jan., Feb. 2008; 86:32-35.
MacDonald; Flea Control: An overview of treatment concepts for North America; Veterinary Dermatology, 1995; 6:121-130.
Malk et al.; Permethrin Spot-On Intoxication of Cats: Literature Review and Survey of Veterinary Practitioners in Australia; Journal of Feline Medicine and Surgery; 2010; 12:5-14.
Junquera; Definition of Flumethrin; http://parasitipedia.net/index.php?option=com_content&view=article&id=2458&Itemid=2726; Printed Nov. 4, 2013; pp. 1-3.
Fernandez-Alvarez et al., "The photochemical behaviour of five household pyrethroid insecticides and a synergist as studied by photo-solid-phase microextraction", Anal. Bioanal. Chem. (2007), 388:1235-1247.
Casas et al., "Effects of sample pretreatment and storage conditions in the determination of pyrethroids in water samples by solid-phase microextraction and gas chromatography-mass spectrometry", Anal. Bioanal. Chem (2007) 387:1841-1849.

* cited by examiner

*Primary Examiner* — Kortney L Klinkel
(74) *Attorney, Agent, or Firm* — Polsinelli PC

(57) ABSTRACT

A spot-on pesticide composition for animals, specifically mammals, including dogs and cats, which composition comprises a combination of active components, including fipronil and a pyrethroid, and optionally an insect growth regulator, in doses and proportions which are parasiticidally effective against a variety of insects and pests, and in a formulation which is convenient for local application to the animal's skin, preferably localized over a small surface area.

31 Claims, No Drawings

SPOT-ON PESTICIDE COMPOSITION

RELATED APPLICATIONS

This patent application is a divisional of U.S. Ser. No. 12/888,123, filed Sep. 22, 2010, which claims the benefit of U.S. Provisional Ser. No. 61/297,154, filed Jan. 21, 2010, and U.S. Provisional Patent Application No. 61/244,788, filed Sep. 22, 2009, all of which are hereby incorporated by reference in their entirety.

FIELD OF THE INVENTION

The present invention relates to a spot-on or pour-on pesticide composition comprising fipronil and a pyrethroid, which combination is useful in the treatment or prevention of insect, parasite, or tick infestations in animals, specifically mammals, including dogs and cats. The present invention further relates to a spot-on or pour-on pesticide composition comprising fipronil, a pyrethroid, and an insect growth regulator, which combination is also useful in the treatment and prevention of insect, parasite, or tick infestations in animals, specifically mammals. The present invention also relates to a method for the localized cutaneous application of a pesticide composition comprising fipronil and a pyrethroid, and additionally an insect growth regulator.

BACKGROUND OF THE INVENTION

Traditional products for the treatment or prevention of insect or parasite infestation of animals include shampoo treatments, insecticidal collars, orally ingested treatments, compositions designed to treat an animal's environment, spot-on treatments, and the like. Different treatment forms offer unique benefits and drawbacks; however, the majority offer substantial disadvantages. For instance, shampoo treatments require that the treatment be applied over the entire surface of the animal and subsequently rinsed off, which is typically unpleasant for both the animal and the owner and only provides a short-term, transient treatment. Insecticidal collars require the animal to physically wear the collar for a period of time often lasting several months, which is uncomfortable and burdensome to the animal. Additional, treatments administered orally tend to increase the possibility of side effect and are more difficult to administer to the animal. Alternatively, treatment of the animal's surroundings and habitat is often undesirable due to the fact that the treatment may cause discoloration of furniture, carpet, bedding, etc., and may also produce unpleasant odors. Thus, it is desirable to have a spot-on treatment that can be applied to the animal in smaller portions, while maintaining treatment efficacy across the entire body surface of the animal.

Spot-on compositions that have been previously developed incorporate a multitude of pesticide agents. Common agents include arylpyrazole derivatives, insect growth regulators, pyrethroids, nodulisporic acid derivatives, neonicotinoids, formamides, avermectins, and the like. All of the compounds listed herein have different mechanisms of action, and accordingly treat and prevent infestation in different manners. Consequently, the various compounds also have a variety of different adverse effects associated with treatment. The various agents may be combined in a variety of concentrations. Generally, higher concentrations of the active components result in higher pest kill rates, and more successful treatments; however, the use of higher concentrations of the active components are more expensive to make and result in a greater likelihood that the animal will suffer adverse effects from treatment. Adverse effects of treatments include skin discoloration, local hair loss, itching, redness, excessive salivation, and in certain cases, neurotoxicity.

The spot-on treatments known within the art generally have a prolonged period of action before the active ingredient(s) effectively eliminates the target pest. For instance, insect growth regulators (i.e. juvenile hormone mimetics) exterminate target pests by effectively inhibiting the development of immature pests, so that they are not able to reproduce. Even though the insect growth regulators are effective in ultimately controlling the pest infestation, additional time is required to kill all pests, which leads to additional time in which the animal host, as well as all other animals and humans, must suffer the effects of the infestation. Even quick-acting agents, such as the arylpyrazole derivative known as fipronil, which causes hyperexcitation of the pest leading to its death, have a prolonged onset of action. Generally, it may take multiple hours for quick-acting agents to provide symptomatic relief to the host animal.

Therefore, given the limitations of the prior art, it would be desirable to have a spot-on pesticide treatment that utilizes low concentrations of known chemicals so as to minimize the risk of adverse effects, has a high pest kill rate, and has an improved kill rate, preferably within the first hour of treatment.

SUMMARY OF THE INVENTION

The invention relates to novel spot-on compositions for treating and preventing insect or tick infestation, as well as a method of killing pests comprising applying the compositions to a host animal, specifically a mammal. The spot-on insecticidal composition of the current invention comprises low concentrations of the active components fipronil and a pyrethroid, and may additionally include an insect growth regulator, in which the active agents are each present in the composition in concentrations generally less than 20% of the total weight of spot-on composition (w/w). Such low concentrations minimize the risk of adverse effects. It has further been discovered that these novel combinations of active components have a higher and faster kill rate of pests (e.g. fleas and ticks) than treatment with fipronil and/or an insect growth regulator alone or without a pyrethroid. The compositions of the present invention further comprise an organic solvent and may optionally include an antioxidant.

One embodiment of the current invention relates to a spot-on composition comprising between about 1% and about 20% (w/w) fipronil, between about 1% and about 20% (w/w) pyrethroid, between about 65% to about 85% (w/w) organic solvent, and between about 2% to about 10% (w/w) antioxidant. More specifically, this particular embodiment of the spot-on composition includes between about 5% and about 15% (w/w) fipronil, between about 2% and about 10% (w/w) pyrethroid, between about 70% to about 80% (w/w) organic solvent, and between about 3% and about 8% (w/w) antioxidant. Most specifically, the first embodiment of the present invention includes between about 8% and about 11% (w/w) fipronil, between about 4% and about 6% (w/w) pyrethroid, between about 75% and about 80% (w/w) organic solvent, and between about 4% and about 6% (w/w) antioxidant.

A second embodiment of the current invention relates to a spot-on composition comprising between about 1% and about 20% (w/w) fipronil, between about 1% and about 20% (w/w) pyrethroid, between about 1% and about 20% (w/w) insect growth regulator, between about 55% and about 80% (w/w) organic solvent, and between about 2% and about 10% (w/w) antioxidant. More specifically, this embodiment of present composition includes between about 5% and about 15% (w/w) fipronil, between about 2% and about 10% (w/w) pyrethroid, between about 4% and about 15% (w/w) insect growth regulator, between about 60% and about 75% (w/w) organic solvent, and between about 3% and about 8% (w/w) antioxidant. Most specifically, the spot-on composition of the present invention includes between about 8% and about 11% (w/w) fipronil, between about 4% and about 6% (w/w) pyrethroid, between about 7% and about 11% (w/w) insect growth regulator, between about 65% and about 70% (w/w) organic solvent, and between about 4% and about 6% (w/w) antioxidant.

A third embodiment of the current invention relates to a spot-on composition comprising between about 1% and about 20% (w/w) fipronil, between about 1% and about 20% (w/w) pyrethroid, and between about 60% to about 85% (w/w) organic solvent. More specifically, this embodiment of the spot-on composition includes between about 5% and about 15% (w/w) fipronil, between about 8% and about 18% (w/w) pyrethroid, and between about 65% and about 80% (w/w) organic solvent. Most specifically, this embodiment of the of the present invention includes between about 8% and about 11% (w/w) fipronil, about 14% and about 16% (w/w) pyrethroid, and between about 70% and about 75% (w/w) organic solvent.

A fourth embodiment of the spot-on composition includes between about 1% and about 20% (w/w) fipronil, between about 1% and about 20% (w/w) pyrethroid, between about 1% and about 20% (w/w) insect growth regulator, and between about 55% and about 75% (w/w) organic solvent. More specifically, this embodiment of present composition includes between about 5% and about 15% (w/w) fipronil, between about 8% and about 18% (w/w) pyrethroid, between about 5% and about 16% (w/w) insect growth regulator and between about 60% and about 70% (w/w) organic solvent. Most specifically, this embodiment of the spot-on composition includes between about 8% and about 11% (w/w) fipronil, between about 14% and about 16% (w/w) pyrethroid, between about 11% and about 14% (w/w) insect growth regulator, and between about 60% and about 65% (w/w) organic solvent.

A fifth embodiment of the spot-on composition includes between about 1% and about 20% (w/w) fipronil, between about 1% and about 20% (w/w) pyrethroid, between about 1% and about 20% (w/w) insect growth regulator, between about 65% and about 85% (w/w) organic solvent, and between about 2% and about 10% (w/w) antioxidant. More specifically, this embodiment of present composition includes between about 5% and about 15% (w/w) fipronil, between about 2% and about 10% (w/w) pyrethroid, between about 2% and about 10% (w/w) insect growth regulator, between about 70% and about 85% (w/w) organic solvent, and between about 3% and about 8% (w/w) antioxidant. Most specifically, the spot-on composition of the present invention includes between about 8% and about 11% (w/w) fipronil, between about 4% and about 6% (w/w) pyrethroid, between about 3% and about 6% (w/w) insect growth regulator, between about 75% and about 80% (w/w) organic solvent, and between about 4% and about 6% (w/w) antioxidant.

A sixth embodiment of the spot-on composition includes between about 1% and about 20% (w/w) fipronil, between about 1% and about 20% (w/w) pyrethroid, between about 1% and about 20% (w/w) insect growth regulator, and between about 55% and about 80% (w/w) organic solvent. More specifically, this embodiment of present composition includes between about 5% and about 15% (w/w) fipronil, between about 8% and about 18% (w/w) pyrethroid, between about 2% and about 10% (w/w) insect growth regulator, and between about 60% and about 75% (w/w) organic solvent. Most specifically, this embodiment of the spot-on composition includes between about 8% and about 11% (w/w) fipronil, between about 14% and about 16% (w/w) pyrethroid, between about 3% and about 6% (w/w) insect growth regulator, and between about 65% and about 70% (w/w) organic solvent.

In addition, the present invention further provides a method of eliminating and preventing pest infestations on an animal, specifically a dog, the method comprising administering a localized cutaneous application of a spot-on composition of the present invention between the two shoulders of the animal in a volume sufficient to deliver a dose of the active components ranging from about 0.5 mg/kg to about 10 mg/kg of animal body weight.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

DETAILED DESCRIPTION OF THE INVENTION

The compositions provided herein are spot-on pesticide compositions that utilize combinations of certain active compounds to treat insect, parasite, or tick infestation of animals, specifically mammals (preferably dogs and cats), and also prevent future infestations by prolonged treatment efficacy that can last up to three months. As such, the compositions exterminate existing pests, and prevent those pests that survive from developing and reproducing. The compositions halt the growth cycle and prevent pests from laying additional eggs. The compositions of the current invention are useful in the treatment of many pests, especially fleas and ticks found on domesticated animals. The compositions include low concentrations of fipronil and a pyrethroid, and may further comprise an insect growth-regulating compound. In addition, the present invention is based in part on the finding that treatment of a host animal with compositions comprising a combination of fipronil and a pyrethroid results in dramatically higher kill rates within the first twenty-four hours of treatment than does treatment with fipronil and an insect growth regulator, alone or combined, without the addition of a pyrethroid.

The spot-on compositions of the present invention include fipronil. The fipronil compound is a phenylpyrazole acaricide with efficacy against a broad spectrum of tick species and was first disclosed in U.S. Pat. No. 5,232,940. Fipronil achieves its efficacy by disrupting the central nervous system by blocking the passage of chloride ions through the GABA receptor and glutamate-gated chloride channels (GluCl), components of the central nervous system. This disruption causes hyperexcitation of contaminated nerves and muscles, which results in eventual death. The compound is a slow-acting acaricide, and as such, can be used to target not only the host, but also other ticks in which the host comes in contact. Fipronil is also known as 5-amino-1-[2,6-dichloro-4-(trifluoromethyl)phenyl]-4-[(1-R,S)(trifluoromethyl)sulfinyl]-1H-pyrazole-3-carbonitrile, 5-amino-1-(2,6-dichloro-α,α,α-trifluoro-p-tolyl)-4-[(trifluoromethyl)sulfinyl]pyrazole-3-carbonitrile, and fluocyanobenpyrazole [CAS No. 120068-37-3]. Fipronil is generally available as either a liquid or solid crystalline substance or powder. Fipronil typically comprises between about 1% and about 20% (w/w) of the total weight of the spot-on composition. In some embodiments, fipronil comprises about 20%, 19%, 18%, 17%, 16%, 15%, 14%, 13%, 12%, 11%, 10%, 9%, 8%, 7%, 6%, 5%, 4%, 3%, 2%, or 1% (w/w) of the spot-on composition. For example, the amount of fipronil present in the spot-on composition may range from between about 5% to about 15% (w/w) of the total composition, and preferably ranges from between about 7% and about 12% (w/w). Most preferably, the amount of fipronil present in the spot-on composition may range from between about 8% and about 11% (w/w) of the total composition. In an exemplary embodiment, the amount of fipronil present in the composition is 9.8% (w/w) of the total composition. The chemical structure for fipronil is shown below.

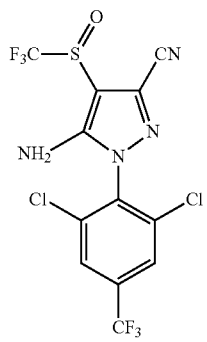 [SMILES: N#Cc1nn(-c2c(Cl)cc(C(F)(F)F)cc2Cl)c(N)c1S(=O)C(F)(F)F]

The spot-on compositions of the present invention also include a pyrethroid compound. Generally, pyrethroids are a class of synthetic insecticides that are related to the naturally-occurring pyrethrins. Pyrethroids tend to be more effective than the natural pyrethrins, and less toxic to mammals. Pyrethroids are axonic poisons that work by keeping the sodium channels open in the neuronal membranes. The sodium channel consists of a membrane protein with a hydrophilic interior which permits sodium ions to enter and exit the membrane. When the sodium channels are kept open, the influx of sodium ions results in hyperexcitation, and the pest becomes paralyzed. The pyrethroid typically comprises between about 1% and about 20% (w/w) of the total weight of the spot-on composition. In some embodiments, the pyrethroid comprises about 20%, 19%, 18%, 17%, 16%, 15%, 14%, 13%, 12%, 11%, 10%, 9%, 8%, 7%, 6%, 5%, 4%, 3%, 2%, or 1 (w/w) of the spot-on composition. For example, the amount of a pyrethroid present in the spot-on composition may range from between about 1% to about 18% (w/w) of the total composition, and preferably ranges from about 3% to about 16% (w/w). In another embodiment, the amount of a pyrethroid present in the spot-on composition may range from about 1% to about 10% (w/w) of the total composition weight. In a further embodiment, the amount of a pyrethroid present in the spot-on composition may range from about 4% to about 6% (w/w) of the total composition. In still another embodiment, the amount of a pyrethroid present in the spot-on composition may range from between about 10% to about 16% (w/w) of the total composition. In a further embodiment, the amount of a pyrethroid present in the spot-on composition may range from between about 14% to about 16% (w/w) of the total composition.

Suitable non-limiting examples of pyrethroids include permethrin, cypermethrin, cyphenothrin, etofenprox, fenvalerate, and cyfluthrin. Specifically, cyphenothrin is classified as a pyrethroid ester insecticide. Cyphenothrin is also known as (RS)-α-cyano-3-phenoxybenzyl(1RS,3RS;1RS,3SR)-2,2-dimethyl-3-(2-methylprop-1-enyl)cyclopropanecarboxylate, d-trans-cyphenothrin, d-cyphenothrin, Gokilaht™, (RS)-α-cyano-3-phenoxybenzyl-(1RS)-cis-trans-2,2-dimethyl-3-(2-methylprop-1-enyl)cyclopropanecarboxylate, (±)-α-cyano-3-phenoxybenzyl (±)-cis-trans-chrysanthemate, and cyano (3-phenoxyphenyl)methyl 2,2-dimethyl-3-(2-methyl-1-propenyl)cyclopropanecarboxylate. Certain commercially available Gokilaht™ products on the market incorporate both cyphenothrin and pyriproxyfen. It should be noted that the cyphenothrin product of the current invention may only incorporate the active compound pyriproxyfen in those formulations not also containing S-methoprene due to the discovery that the incorporation of both S-methoprene and pyriproxyfen in a composition decreases efficacy and increases the likelihood of adverse effects. The chemical structure for cyphenothrin is shown below.

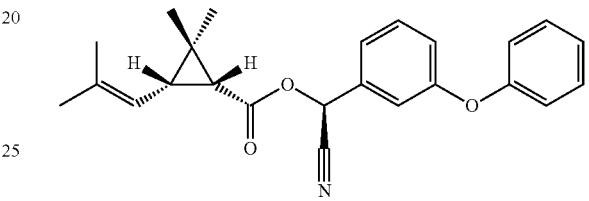

In one preferred embodiment, the amount of cyphenothrin present in the spot-on composition effective for the treatment of pest infestations in dogs is 5.0% (w/w) of the total composition. In a further preferred embodiment, the amount of cyphenothrin present in the spot-on composition effective for the treatment of pest infestations in dogs is 8.2% (w/w) of the total composition.

Etofenprox is also known as ethofenprox, ethophenprox, 1-ethoxy-4-[2-methyl-1-[[3-(phenoxy)phenyl]methoxy]propan-2-yl]benzene 2-(4-Ethoxyphenyl)-2-methylpropyl 3-phenoxybenzyl ether, 3-Phenoxybenzyl 2-(4-ethoxyphenyl)-2-methylpropyl ether, C076840, 2-(4-ethoxyphenyl)-2-methylpropyl-3-phenoxybenzyl ether, 1-((2-(4-Ethoxyphenyl)-2-methylpropoxy)methyl)-3-phenoxy benzene, alpha-((p-Ethoxy-beta,beta-dimethylphenethyl)oxy)-m-phenoxytoluene. The CAS Registration number for etofenprox is 80844-07-1. Etofenprox is known to be an effective pyrethroid for the elimination of pests in cats. The chemical structure for etofenprox is shown below.

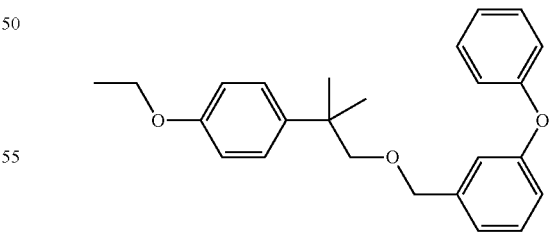

In an exemplary embodiment, the amount of etofenprox present in the spot-on composition effective for the treatment of pest infestations in cats is 15.0% (w/w) of the total composition.

The spot-on pesticide composition of the current invention may additionally include an insect growth regulator (IGR). IGRs are not effective in killing pre-existing pests; they prevent reproduction and further infestation. An IGR is generally a compound that is capable of disrupting the growth and development of pest species, so that the pest cannot mature and reproduce. The IGR typically comprises less than about 20% (w/w) of the total weight of the spot-on composition. In some embodiments, the IGR comprises about 19%, 18%, 17%, 16%, 15%, 14%, 13%, 12%, 11%, 10%, 9%, 8%, 7%, 6%, 5%, 4%, 3%, 2%, 1%, 0.1%, or 0% (w/w) of the spot-on composition. For example, the amount of IGR present in the spot-on composition may range from between 0% to about 20% (w/w) of the total composition weight, and preferably the IGR ranges from between about 2% to about 15% (w/w) of the total composition. In another embodiment, the amount of IGR present in the spot-on composition may range from about 4% to about 12% (w/w) of the total composition. In a further embodiment, the amount of IGR present in the spot-on composition may range from about 7% to about 14% (w/w) of the total composition. In still another embodiment, the amount of IGR may range from between about 8% to about 12% (w/w) of the total composition. In an additional embodiment, the amount of IGR may range from between about 2% to about 9% (w/w) of the total composition. In a further embodiment, the amount of IGR may range from between about 3% to about 5% (w/w) of the total composition.

IGRs may include, but are not limited to juvenile hormone mimics, chitin synthesis inhibitors, and the like. Suitable non-limiting examples of insect growth regulators include bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron, triflumuron, epofenonane, fenoxycarb, hydroprene, kinoprene, methoprene, pyriproxyfen, triprene, and combinations thereof. In a preferred embodiment, the insect growth regulator is S-methoprene.

Generally, methoprene is a racemic mixture of the R- and S-enantiomers of the compound, however, only the S-enantiomer is active as a juvenile hormone analog. A juvenile hormone analog exerts a therapeutic effect by mimicking the natural juvenile hormones found within pests. Juvenile hormone must be absent for a pupa to molt to an adult, so methoprene treated larvae are unable to successfully develop from pupa to an adult pest. This action breaks the natural life cycle of the pest, preventing it from maturing and reproducing. S-methoprene is also known as isopropyl (2E,4E,7S)-11-methoxy-3,7,11-trimethyl-2,4-dodecadienoate. S-methoprene is available in a variety of commercial products and is useful in controlling long-term pest infestation, while other active components are primarily effective in the immediate, short-term elimination of pests. The pest kill time for treatment with S-methoprene will vary depending on the typical duration of life for the species being treated. Unlike some other compounds, S-methoprene is generally considered non-toxic to humans, which has led to its use in the treatment of well cisterns and a number of food items, including meat, milk, mushrooms, peanuts, rice, and cereals. In an exemplary embodiment, the concentration of S-methoprene present in the spot-on composition effective for the treatment of pest infestations in animals is 8.8% (w/w).

In an alternative embodiment (i.e. those embodiments of the present invention that do not contain S-methoprene), the insect growth regulator may be the juvenile hormone analog pyriproxyfen, also known as 4-phenoxyphenyl 2-(2-pyridyloxy)propyl ether and Nylar™. The chemical structure for pyriproxyfen is shown below.

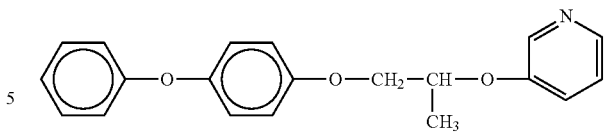

In an exemplary embodiment, the amount of pyriproxyfen present in the spot-on composition effective for the treatment of pest infestations in animals is 2.0% (w/w) of the total composition.

The spot-on compositions of the present invention, which are non-aqueous, also comprise an organic solvent. Generally, the organic solvent is defined as a carbon-containing chemical that is capable of dissolving a solid, liquid, or a gas. Although one skilled in the art will appreciate that a wide variety of solvents may be incorporated into the current invention, the solvents should generally have a dielectric constant ranging from about 1 to 40, a low boiling point (less than 100° C.), have a density less than the density of water (less than 1.0 at 20° C.), and generally be soluble with water. In addition, the organic solvent should cause minimal cutaneous irritation when applied to the skin of an animal, including a dog or cat. Suitable examples of organic solvents include, but are not limited to, acetyltributyl citrate, fatty acid esters such as dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, diethylene glycol monoethyl ether, monomethylacetamide, dipropylene glycol monomethyl ether, liquid polyoxyethylene, glycols, propylene glycol, 2-pyrrolidones such as N-methylpyrrolidone, diethylene glycol monoethyl ether, ethylene glycol, diethyl phthalate, ethoxydiglycol, or combinations thereof. In a preferred embodiment, the organic solvent comprises diethylene glycol monoethyl ether.

In addition, the organic solvent generally comprises between about 55% to about 85% (w/w) of the spot-on composition. In some embodiments, the organic solvent comprises about 85%, about 80%, about 75%, about 70%, about 65%, about 60%, or about 55% (w/w) of the total composition. For example, the amount of organic solvent present in the spot-on composition preferably ranges from between about 60% to about 80% (w/w) of the composition. In another embodiment, the amount of organic solvent in the spot-on composition ranges from between about 60% to about 75% (w/w) of the total composition. In an additional embodiment, the amount of organic solvent in the spot-on composition ranges from between about 70% to 80% (w/w) of the total composition. In still another embodiment, the amount of organic solvent in the spot-on composition ranges from between about 60% to 70% (w/w).

The spot-on composition may further include an antioxidant. An antioxidant can generally be defined as a compound capable of slowing or preventing the oxidation of other molecules. Oxidation is a chemical reaction that transfers electrons from the original substance to an oxidizing agent. Oxidation reactions can produce free radicals, which start chain reactions that damage cells. Antioxidants terminate these chain reactions by removing free radical intermediates, and inhibit other oxidation reactions by being oxidized themselves. Within the spot-on composition, the antioxidant acts as a stabilizer, preventing the various components from degrading by oxidation processes. In addition, many of the commercially-available compositions that incorporate a pyrethroid, including cyphenothrin have reported that the animals suffer from adverse effects including paraesthesia (a skin sensation that generally comprises feelings of prickling, itching, and tingling). However, it has been shown that inclusion of an antioxidant into the spot-on composition helps to prevent the undesirable adverse effects associated with treatment regimens that include cyphenothrin, as undesirable in U.S. Ser. No. 12/876,122 entitled LIQUID PEST CONTROL FORMULATION, which is Commonly owned and is incorporated herein by reference. It should be noted that the spot-on compositions of the present invention do not include crystallization inhibitors.

Antioxidants incorporated into the current invention should generally be miscible with the organic solvents described herein. The antioxidant also should not cause irritation to the skin of an animal, specifically a dog or cat, when applied to the animal's skin. In addition, the antioxidant may be natural or synthetic. Suitable antioxidants include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxanthin, alpha-carotene, beta-carotene, beta-carotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytyrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives, vitamin Q10, wheat germ oil, zeaxanthin, or combinations thereof. One skilled in the art will appreciate that the antioxidants incorporated into the composition (including those listed herein) encompass all potential salt and ester forms of the antioxidants in addition to the pure forms of the compound. Preferably, the antioxidant comprises a vitamin E compound and may be selected from the group consisting of tocopherol acetate, tocopherol linoleate, tocopherol nicotinate, tocopherol succinate, ascorbyl tocopherol phosphate, dioleyl tocopherol methylsilanol, tocophersolan, tocopherol linoleate/oleate, and combinations thereof. In an exemplary embodiment, the antioxidant comprises tocopherol nicotinate [CAS No. 43119-47-7].

In addition, the antioxidant typically comprises less than about 10% (w/w) of the total spot-on composition. In some embodiments, the antioxidant comprises about 9%, 8%, 7%, 6%, 5%, 4%, 3%, 2%, 1%, 0.1%, or 0% (w/w) of the total composition. For example, the amount of antioxidant present in the spot-on composition may range from between 2% to about 10% (w/w) of the total composition, and preferably the antioxidant ranges from between about 3% to about 6% (w/w) of the total composition. In a further embodiment, the amount of antioxidant present in the spot-on composition ranges from between about 4% to about 6% (w/w) of the total composition. In an exemplary embodiment, the amount of antioxidant present in the composition is 5.3% (w/w).

The spot-on composition may further include inactive excipients that are added to the composition as a result of their incorporation into the individual active components. For instance, the fipronil component of the composition may be provided in a 95% solution, meaning that 95% of the fipronil component volume is active fipronil compound and the remaining 5% constitutes inactive excipients that are consequently introduced into the composition, as such the pesticide may not be 100% pure concentrate and may be purchased with other constituents. One skilled in the art will recognize that the inactive excipients include, but are not limited to binders, fillers, non-effervescent disintegrants, effervescent disintegrants, preservatives, diluents, lubricants, pH modifiers, stabilizers, and the like. It should, however, be understood that the inactive excipients are typically incorporated as a portion of the active ingredient components and comprise a small percentage (generally less than 1%) of the total spot-on composition volume, generally not affecting the physical characteristics of the spot-on composition.

It should be understood that the active components of the spot-on composition may be provided in the form of pure concentrate (100% concentration) or a diluted composition with additional excipients in the dosage form (i.e. the amount of active ingredient in the composition is less than or equal to 99.99%, and the remainder consists of inactive excipients). One of skill in the art will appreciate that the volume of active component added to the spot-on composition will need to be adjusted to account for the dilution and to ensure the end spot-on composition comprises the appropriate final concentration of each of the active components. One of skill in the art will also appreciate that the various components of the spot-on composition may be provided in a variety of dosage forms including, but not limited to powder, briquettes, liquid solution or suspension, pellets, emulsion, aerosol, cream, gel, ointment, and the like.

Additionally, the spot-on pesticide composition of the current invention can be produced by contacting the various active components of the spot-on composition with one another to produce a spot-on formulation suitable for application to an animal's skin. It should be understood that the current invention encompasses a variety of physical formulations; however, the spot-on compositions of the current invention are generally directed to liquid solutions and suspensions. The formulations of the present invention may be prepared by standard techniques known in the art. For instance, in one embodiment where the desired spot-on formulation is a liquid solution, the composition is produced by bringing the fipronil and pyrethroid components into contact with a solvent system and then gently heating and stirring the components until dissolved. In a preferred embodiment, the spot-on composition comprising fipronil, a pyrethroid, and a solvent system may further be contacted with an antioxidant, and the combination is then stirred to create a spot-on composition. A person having ordinary skill in the art will appreciate that the various components of the spot-on composition may be contacted and mixed with one another in any order desired, so long as solution is adequately stirred and mixed.

The physical characteristics of the spot-on composition may vary depending upon the physical characteristics desired. However, the spot-on composition should be capable of application to the skin of an animal and provide adequate stasis to allow the active components of the spot-on composition to be absorbed by the host animal. Preferably, the spot-on compositions of the present invention have low viscosity. Viscosity is the measurement of flow resistance due to internal friction within the fluid, and is measured in centistokes (cSt). A lower cSt measurement means the fluid will flow with less resistance, because of minimal molecular friction within the fluid. The lower the viscosity the faster the fluid will flow. High viscosity substances are liquids that are thick and gelatinous in nature with slow flow. Low viscosity substances exhibit a fast flow with an example being water at room temperature (water at 20° C. has a viscosity of about 1 cSt; 1 cSt=1 mm$^2$/second). The spot-on compositions of the present invention typically have a viscosity ranging from about 0.01 mm$^2$/second to about 100 mm$^2$/second. In a more preferred embodiment, the spot-on composition has a viscosity ranging from about 1 mm$^2$/second to about 30 mm$^2$/second. In a further preferred embodiment, the spot-on composition has a viscosity ranging from about 4 mm$^2$/second to about 20 mm$^2$/second.

The basic spot-on composition of the present invention includes fipronil at a concentration ranging between about 1% and about 20% (w/w), a pyrethroid at a concentration ranging between about 1% and about 20% (w/w), and an organic solvent at a concentration ranging between about 55% and about 85% (w/w) of the total spot-on composition. For the basic spot-on composition, it is preferable to use between about 8% to about 11% (w/w) fipronil, about 3% to about 16% (w/w) pyrethroid, and about 60% to about 80% (w/w) organic solvent, depending on the type of animal to be treated. The basic spot-on composition may also additionally include an IGR at a concentration ranging between 1% and about 20% (w/w) of the composition, preferably at a concentration ranging between about 2% to about 12% (w/w) of the total composition. More preferably, the IGR is present in the composition at a concentration ranging between 4% and 12% (w/w) of the total composition. In addition, the basic spot-on composition may further include an antioxidant at a concentration ranging between 0% and about 10% (w/w) of the total composition, preferably at a concentration ranging between about 4% and about 6% (w/w) of the total composition.

In a preferred embodiment the present invention provides a spot-on composition comprising 9.97% (w/w) fipronil, 5.3% (w/w) cyphenothrin, 79.43% (w/w) diethylene glycol monoethyl ether, and 5.3% (w/w) tocopherol nicotinate. This spot-on composition can be used to treat any mammal, but it is very desirable for treating dogs.

Another preferred embodiment of the present invention comprises a spot-on composition comprising 9.97% (w/w) fipronil, 5.3% (w/w) cyphenothrin, 9.21% (w/w) S-methoprene, 70.22% (w/w) diethylene glycol monoethyl ether, and 5.3% (w/w) tocopherol nicotinate. This spot-on composition can be used to treat any mammal, but it is very desirable for treating dogs.

In yet another preferred embodiment the present invention provides a spot-on composition comprising 9.97% (w/w) fipronil, 15.89% (w/w) etofenprox, and 74.14% (w/w) diethylene glycol monoethyl ether. This spot-on composition can be used to treat any mammal, but it is very desirable for treating cats.

In yet another preferred embodiment the present invention provides a spot-on composition comprising 9.97% (w/w) fipronil, 15.89% (w/w) etofenprox, 12.36% (w/w) S-methoprene, and 61.78% (w/w) diethylene glycol monoethyl ether. This spot-on composition can be used to treat any mammal, but it is very desirable for treating cats.

In yet another preferred embodiment the present invention provides a spot-on composition comprising 9.97% (w/w) fipronil, 5.3% (w/w) cyphenothrin, 4% (w/w) pyriproxyfen, 75.43% (w/w) diethylene glycol monoethyl ether, and 5.3% (w/w tocopherol nicotinate. This spot-on composition can be used to treat any mammal, but it is very desirable for treating dogs.

In yet another preferred embodiment the present invention provides a spot-on composition comprising 9.97% (w/w) fipronil, 15.89% (w/w) etofenprox, 4.4% (w/w) pyriproxyfen, and 69.74% (w/w diethylene glycol monoethyl ether. This spot-on composition can be used to treat any mammal, but it is very desirable for treating cats.

In addition, the current invention further embodies a method of killing pest pupae and adults on an animal comprising administering a localized cutaneous application between the shoulders of the animal, a spot-on composition comprising between about 1% to 20% (w/w) fipronil and between about 1% to 20% (w/w) pyrethroid. The method of the using the composition of the present invention preferably involves the localized administration of the basic spot-on composition, which composition preferably comprises between 7% (w/w) to about 12% (w/w) fipronil and about 3% to about 16% (w/w) pyrethroid, and may additionally include an IGR preferably at a concentration range from between about 4% to about 12% (w/w) of the total composition.

The compositions and method according to this invention are intended for application to animals, in particular dogs and cats, and are generally applied by deposition onto the skin ("spot-on" or "pour-on" application). Treatment typically comprises a localized application over a surface area of less than 10 cm$^2$, especially of between 5 and 10 cm$^2$. Generally, the spot-on composition should be applied to an area where the animal cannot lick the application area, as licking of the application area may lead to transient adverse effects, such as excessive salivation. In particular, application is preferred at two points and preferably localized between the animal's shoulders. After the spot-on composition has been applied, the composition diffuses, in particular over the animal's entire body, and then dries without crystallizing or modifying the appearance (in particular absence of any whitish deposit or dusty appearance) or the feel of the animal's fur. Further, the method of the current invention is directed to application of the spot-on composition to the skin of the animal every four weeks to ensure continuous treatment and prevention of pest infestation. Typically, the active constituents are applied to the host animal together in a single formulation.

In a preferred embodiment of the invention, the method of killing insect and pest pupae and adults on an animal, comprises administering a localized cutaneous application between the shoulders of an animal, a spot-on composition comprising 9.97% (w/w) fipronil, 5.3% (w/w) cyphenothrin, 79.43% (w/w) diethylene glycol monoethyl ether, and 5.% (w/w) tocopherol nicotinate. This method can be used to treat any animal, but it is very desirable for treating dogs.

Another preferred embodiment of the present invention comprises a method of killing insect and pest pupae and adults on a dog or cat, comprising administering a localized cutaneous application between the shoulders of an animal, a spot-on composition comprising 9.97% (w/w) fipronil, 5.3% (w/w) cyphenothrin, 9.21% (w/w) S-methoprene, 70.22% (w/w) diethylene glycol monoethyl ether, and 5.3% (w/w) tocopherol nicotinate. This method can be used to treat any animal, but it is very desirable for treating dogs.

In yet another preferred embodiment the present invention provides a method of killing insect and pest pupae and adults on an animal, comprising administering a localized cutaneous application between the shoulders of an animal, of a spot-on composition comprising 9.97% (w/w) fipronil, 15.89% (w/w) etofenprox, and 74.14% (w/w) tocopherol nicotinate. This method can be used to treat any animal, but it is very desirable for treating cats.

In yet another preferred embodiment the present invention provides a method of killing insect and pest pupae and adults on an animal, comprising administering a localized cutaneous application between the shoulders of an animal, a spot-on composition comprising 9.97% (w/w) fipronil, 15.89% (w/w) etofenprox, 12.36% (w/w) S-methoprene, and 77.67% (w/w) diethylene glycol monoethyl ether. This method can be used to treat any animal, but it is very desirable for treating cats.

In yet another preferred embodiment the present invention provides a method of killing insect and pest pupae and adults on an animal, comprising administering a localized cutaneous application between the shoulders of an animal, a spot-on composition comprising 9.97% (w/w) fipronil, 5.3% (w/w) cyphenothrin, 4.0% (w/w) pyriproxyfen, 75.43% (w/w) diethylene glycol monoethyl ether, and 5.3% (w/w) tocopherol nicotinate. This method can be used to treat any animal, but it is very desirable for treating dogs.

In yet another preferred embodiment the present invention provides a method of killing insect and pest pupae and adults on an animal, comprising administering a localized cutaneous application between the shoulders of an animal, a spot-on composition comprising 9.97% (w/w) fipronil, 15.89% (w/w) etofenprox, 4.4% (w/w) pyriproxyfen, and 85.63% (w/w) diethylene glycol monoethyl ether. This method can be used to treat any animal, but it is very desirable for treating cats.

In an alternative embodiment, the method of killing insects is carried out such that the spot-on composition is applied in a volume sufficient to deliver a dosage of the active component fipronil ranging from about 0.1 mg/kg to about 40 mg/kg of host animal body weight. In a preferred embodiment, the dose of fipronil ranges from about 2 mg/kg to about 20 mg/kg of host animal body weight. In a more preferred embodiment, the spot-on composition application comprises a volume sufficient to deliver a fipronil dose ranging from about 5 mg/kg to about 15 mg/kg of host animal weight.

In another embodiment, the method of killing insects is carried out such that the spot-on composition is applied in a volume sufficient to deliver a dosage of the active pyrethroid component ranging from about 0.1 mg/kg to about 40 mg/kg of host animal body weight. In a preferred embodiment, the dose of pyrethroid ranges from about 0.5 mg/kg to about 20 mg/kg of host animal body weight. In a more preferred embodiment, the spot-on composition application comprises a volume sufficient to deliver a pyrethroid dose ranging from about 0.5 mg/kg to about 10 mg/kg of host animal body weight.

In a further embodiment, the method of killing insects is carried out such that the spot-on composition further comprises an IGR, and is applied in a volume sufficient to deliver a dosage of the insect growth regulating active component ranging from about 0.1 mg/kg to about 40 mg/kg of host animal body weight. In a preferred embodiment, the dose of insect growth regulator ranges from about 0.2 mg/kg to about 20 mg/kg of host animal body weight. In a more preferred embodiment, the spot-on composition application comprises a volume sufficient to deliver an insect growth regulator dose ranging from about 0.5 mg/kg to about 10 mg/kg of host animal body weight.

One of skill in the art will understand that the dosage ranges provided above are approximate values that may vary within a broad range. The variance in dose is due to the fact that, in practice, the spot-on composition will be administered in defined doses and volumes to animals within a certain range of weights. As a result, the dosage actually applied to the animal may vary by a factor ranging from 0.1 to 10 relative to the preferred dose, without imparting any additional risks pertaining to toxicity or decreased efficacy.

Although the components of the composition are effective against a wide variety of pests and parasites, the composition is especially developed for the treatment of fleas (including the *Ctenocephalides* species) and ticks (the *Rhipecephalus, Ixodes*, and *Trichodectes* species). Furthermore, the frequency of application may be varied according to the needs of the individual animal, as well as the severity of infestation. The treatment of fleas may be repeated as often as once weekly, or may be reserved for one-time acute treatments of flea infestation or flare-ups. In one embodiment of the current invention, the treatment of fleas may be repeated about every four weeks, five weeks, or six weeks. In another embodiment, the spot-on composition is applied to the host animal for a one-time treatment of the pest infestation. With regard to the treatment of ticks, the application schedule for the spot-on composition will vary depending on the type of tick being treated. It is generally recommended that treatment of paralytic ticks (*Ixodes* species) occur more frequently than other species. In an embodiment of the current invention, paralytic ticks are treated at a frequency ranging from one to four weeks, with treatment every two weeks being preferred. Other genera of ticks generally have a treatment schedule similar to treatment of flea infestation, preferably ranging from approximately four to six weeks. In another embodiment, the spot-on composition is applied on a one-time basis for the treatment of tick infestation.

Although the invention described herein is susceptible to various modifications and alternative iterations, specific embodiments thereof have been described in greater detail above. It should be understood, however, that the detailed description of the spot-on composition is not intended to limit the invention to the specific embodiments disclosed. Rather, it should be understood that the invention is intended to cover all modifications, equivalents, and alternatives falling within the spirit and scope of the invention as defined by the claim language.

Definitions

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight and is used to describe the concentration of a particular substance in a mixture or solution.

As used herein, the term "mL/kg" designates milliliters of composition per kilogram of body weight.

As used herein, the term "a.i." designates active ingredient.

As used herein, the term "treatment" or "treating" of a condition, such as pest infestation, includes inhibiting an existing condition or arresting its development; or ameliorating or causing regression of the condition. The term "preventing" or "prevention" of a condition, such as insect or pest infestation, includes substantially blocking or inhibiting the development or growth of a condition before it starts. Compositions that treat or prevent infestations herein will preferably exhibit at least 90% efficacy.

As used herein, the term "pesticide" or "pesticidal" refers to an agent or a composition comprising an agent that is capable of preventing, reducing or eliminating pest infestations. Preferred pesticides of the present invention include fipronil, cyphenothrin, and etofenprox.

As used herein, the term "insect growth regulator" or "IGR" refers to an agent that is capable of interrupting or inhibiting the life cycle of a pest such that the pest never matures into an adult and becomes incapable of reproducing. Preferred IGRs of the present invention include S-methoprene and pyriproxyfen.

As used herein, the term "animal" refers to a mammal, specifically a companion animal, including but not limited to dogs, cats, rabbits, ferrets, horses, and hamsters.

As used herein, the term "pest" and "insect" refers to any ectoparasite, including but not limited to fleas, ticks, flies, keds, mosquitoes, and mites.

The following examples are intended to further illustrate and explain the present invention. The invention, therefore, should not be limited to any of the details in these examples.

EXAMPLE 1

Method of Making a Fipronil/Cyphenothrin Spot-on Pesticide Composition for Dogs

A spot-on pesticide composition was made according to the formulation provided in Table 1:

TABLE 1

Spot-On Pesticide Composition Comprising Fipronil and Cyphenothrin

| Ingredient | Amount for 1000 L |
| --- | --- |
| Fipronil tech. (As 100%) | 98 kg (99.7 kg as 98.3%) |
| Cyphenothrin (As 100%) | 50 kg (53 kg as 94.4%) |
| Tocopherol Nicotinate | 53 kg |
| Diethylene glycol monoethyl ether | Up to 1000 L (about 794.3 kg) |

The diethylene glycol monoethyl ether and the tocopherol nicotinate were charged to a vessel and heated to a temperature of 50° C. (about 1 hour). Once heated, the fipronil and the cyphenothrin were charged to the vessel and all components were mixed until homogenous solution was formed (about 1 hour).

EXAMPLE 2

Method of Making a Fipronil/S-Methoprene/Cyphenothrin Spot-on Pesticide Composition for Dogs A spot-on pesticide composition was made according with the formulation provided in Table 2:

TABLE 2

Spot-On Pesticide Composition Comprising Fipronil, Cyphenothrin, and S-Methoprene

| Ingredient | Amount for 1000 L |
| --- | --- |
| Fipronil tech. (As 100%) | 98 kg (99.7 kg as 98.3%) |
| S-methoprene (As 100%) | 88 kg (92.1 kg as 95.5%) |
| Cyphenothrin (As 100%) | 50 kg (53 kg as 94.4%) |
| Tocopherol Nicotinate | 53 kg |
| Diethylene glycol monoethyl ether | Up to 1000 L (about 702.2 kg) |

The diethylene glycol monoethyl ether and the tocopherol nicotinate were charged to a vessel and heated to a temperature of 50° C. (about 1 hour). Once heated, the fipronil, the cyphenothrin, and the S-methoprene were charged to the vessel and all components were mixed until a homogenous solution was formed (about 1 hour).

EXAMPLE 3

Method of Making a Fipronil/Etofenprox Spot-On Pesticide Composition for Cats

A pesticide composition was made according with the formulation provided in Table 3:

TABLE 3

Spot-On Pesticide Composition Comprising Fipronil and Etofenprox

| Ingredient | Amount for 1000 L |
| --- | --- |
| Fipronil tech. (As 100%) | 98 kg (99.7 kg as 98.3%) |
| Etofenprox (As 100%) | 150 kg (158.9 kg as 94%) |
| Diethylene glycol monoethyl ether | Up to 1000 L (about 741.4 kg) |

The diethylene glycol monoethyl ether was charged to a vessel and heated to a temperature of 50° C. (about 1 hour). Once heated, the fipronil and the etofenprox were charged to the vessel and all components were mixed until a homogenous solution was formed (about 1 hour).

EXAMPLE 4

Method of Making a Fipronil/Etofenprox/S-Methoprene Spot-on Pesticide Composition for Cats A pesticide composition was made according with the formulation provided in Table 4:

TABLE 4

Spot-On Pesticide Composition Comprising Fipronil, Etofenprox, and S-Methoprene

| Ingredient | Amount for 1000 L |
| --- | --- |
| Fipronil tech. (As 100%) | 98 kg (99.7 kg as 98.3%) |
| Etofenprox (As 100%) | 150 kg (158.9 kg as 94%) |
| S-methoprene (As 100%) | 88 kg (123.6 kg as 95.5%) |
| Diethylene glycol monoethyl ether | Up to 1000 L (about 617.8 kg) |

The diethylene glycol monoethyl ether was charged to a vessel and heated to a temperature of 50° C. (about 1 hour). Once heated, the fipronil, the etofenprox, and the S-methoprene were charged to the vessel and all components were mixed until a homogenous solution was formed (about 1 hour).

EXAMPLE 5

Efficacy Evaluation of a Spot-on Composition Containing Fipronil Compared to a Spot-On Composition Containing Fipronil and Cyphenothrin for the Treatment of Fleas and Ticks on Dogs A double blind, controlled study was performed to illustrate the difference in kill rates for ticks and fleas between treatment with a spot-on composition containing fipronil and cyphenothrin prepared in a similar manner to Example 1, and a composition comprising only fipronil.

A total of 18 dogs were randomized into one of three treatment groups. Group A, which was the control group, did not receive any treatment for fleas and ticks and was used as a point of comparison against the active treatment regimens. Group B comprised an active treatment group that received treatment with the fipronil/cyphenothrin spot-on composition combination of 8.38% (w/w) fipronil and 4.76% (w/w) cyphenothrin. Finally, Group C comprised an active treatment group that received treatment with 8.8% (w/w) fipronil only. For all active treatments, a spot-on application was developed and applied to the dogs in a manner in accordance with this invention. All dogs admitted into the experiment were first deemed to be suffering from both flea and tick infestation. The experiment was designed such that all treatment groups were administered the appropriate treatment and then observed at one hour and at four hours after application. During the post-application observation periods, the dogs were contacted with a piece of test paper in defined areas of the dog's body, for a defined period of time. The paper was designed such that dead ticks and fleas would adhere to the paper, and the number of dead ticks and fleas could be counted for comparison to the Group A (control group), to determine the reduction in pests following treatment. In addition, the number of ticks and fleas remaining on the dog, within the observation areas, was also calculated.

The dogs of each group (Group A, Group B, and Group C) were infested with fleas and ticks on Day −1, and the two active treatment groups (Group B and Group C) subsequently received treatment on Day 0. The protocol was designed to test the efficacy of the two treatments in regard to subsequent infestation after an initial treatment with an active spot-on composition. After the initial infestation, the dogs were again infested with fleas in four intervals on the first day of each week (Day 7, 14, 21, and 28) for a period of approximately 4 weeks, with monitoring through Day 30. For each subsequent infestation, the dogs of each treatment group were monitored to determine the kill rates for fleas (*Ctenophalides felis*) and ticks (*Rhipicephalus sanguineus*) at one hour after infestation, four hours after infestation, one day (24 hours) after infestation, and two days (48 hours) after infestation. The values in Tables 5 and 6 represent the average percentage reduction in the number of ticks and fleas, respectively, present on the dogs in each treatment group after subsequent infestations, comparing treatment results for Group B (fipronil and cyphenothrin) with Group C (fipronil). Table 5 provides information on the average tick kill rates for the two active treatment groups (Group B and Group C) described above.

TABLE 5

Group Mean Efficacy Against Ticks

| Day | Time (hrs) | Group B | Group C |
|---|---|---|---|
| 0 | 1 | 31% | 5% |
|  | 4 | 69% | 27% |
|  | 24 | 87% | 86% |
|  | 48 | 96% | 97% |
| 7 | 1 | 95% | 38% |
|  | 4 | 94% | 89% |
|  | 24 | 100% | 100% |
|  | 48 | 100% | 100% |
| 14 | 1 | 40% | 5% |
|  | 4 | 91% | 85% |
|  | 24 | 100% | 99% |
|  | 48 | 100% | 100% |
| 21 | 1 | 98% | 74% |
|  | 4 | 99% | 94% |
|  | 24 | 100% | 100% |
|  | 48 | 100% | 100% |
| 28 | 1 | 96% | 65% |
|  | 4 | 100% | 93% |
|  | 24 | 100% | 100% |
|  | 48 | 100% | 100% |

As indicated in Table 5, the dogs in Group B, who had been treated with a combination of 8.38% fipronil and 4.76% cyphenothrin, experienced significantly greater average tick kill rates at one hour and four hours after treatment (Day 0) and after all re-infestation periods (Days 7, 14, 21, and 28), compared to the Group C dogs who had been treated only with 8.8% fipronil. Thus, Table 5 illustrates that treatment with a combination of fipronil and cyphenothrin results in significantly greater average kill rates and speed of kill for ticks at one hour and four hours after an initial treatment and after subsequent re-infestations. Table 5 also illustrates that treatment with a combination of fipronil and cyphenothrin provides prolonged efficacy for the treatment and prevention of tick infestation up to thirty days following application of the pesticidal composition.

TABLE 6

Group Mean Efficacy Against Fleas

| Day | Time (hrs) | Group B | Group C |
|---|---|---|---|
| 0 | 1 | 26% | 9% |
|  | 4 | 68% | 35% |
|  | 24 | 100% | 100% |
|  | 48 | 100% | 100% |
| 7 | 1 | 91% | 44% |
|  | 4 | 97% | 93% |
|  | 24 | 100% | 100% |
|  | 48 | 100% | 100% |
| 14 | 1 | 85% | 42% |
|  | 4 | 46% | 37% |
|  | 24 | 100% | 100% |
|  | 48 | 100% | 100% |
| 21 | 1 | 89% | 72% |
|  | 4 | 94% | 92% |
|  | 24 | 100% | 100% |
|  | 48 | 100% | 100% |
| 28 | 1 | 69% | 12% |
|  | 4 | 93% | 76% |
|  | 24 | 100% | 100% |
|  | 48 | 100% | 100% |

As is evident from Table 6, the dogs treated with a combination of 8.38% fipronil and 4.76% cyphenothrin (Group B) experienced higher average flea kill rates one hour and four hours after infestation for all subsequent infestation periods (Days 7, 14, 21, and 28). At all re-infestation intervals, the dogs treated with fipronil and cyphenothrin (Group B) experienced greater average reductions in the number of fleas present at one and four hours post re-infestation than the dogs in Group C. Thus, the results of this example illustrate that treatment with a combination of fipronil and cyphenothrin results in significantly greater average kill rates and speed of kill for fleas at one hour and four hours after treatment, and also after subsequent infestations, and provides prolonged treatment efficacy for up to thirty days following treatment.

The empirical data presented in Tables 5 and 6 illustrate that treatment with a combination of fipronil and cyphenothrin results in greater average kill rates and speed of kill for fleas and ticks one hour and four hours after treatment compared to treatment with fipronil alone. In addition, Tables 5 and 6 show that superior kill rates with the combination of fipronil and cyphenothrin persisted after four subsequent re-infestations of the host dogs with both fleas and ticks, up to thirty days after the initial application of the spot-on composition.

EXAMPLE 6

Efficacy Evaluation of a Spot-On Composition Containing Fipronil, S-Methoprene and Cyphenothrin Compared to a Spot-on Composition Containing Fipronil and S-methoprene for the Treatment of Fleas and Ticks on Dogs A double blind, randomized, single-centered, controlled study was performed to illustrate the efficacy of a fipronil and S-methoprene spot-on composition enhanced with cyphenothrin prepared in a similar manner to Example 2, compared to fipronil and S-methoprene spot-on compositions not enhanced with cyphenothrin in the treatment of ticks and fleas on dogs.

The study was conducted on thirteen groups of dogs, each group consisting of six dogs for a total of 78 dogs. Dogs were ranked according to body weight and randomly allocated to four body weight categories: A (4 lbs to 22.9 lbs), B (23 lbs to 44.9 lbs), C (45 lbs to 88.9 lbs), and D (25 lbs to 35.9 lbs). Control dogs (Group 1) were selected to be representative of low, medium, and high body weights and had acceptable numbers of fleas and ticks without being biased toward high parasite numbers. Within each weight category (A, B, C, D) the dogs were randomly allocated to one of three groups (2, 3, or 4), thus forming three groups within each weight category (i.e., 2A, 2B, 2C, 2D, 3A, 3B, 3C, 3D, 4A, 4B, 4C, and 4D). Three spot-on formulations were topically administered, one to each group of dogs in each weight category (Groups 2, 3, and 4) as shown in Table 7.

The fipronil and S-methoprene spot-on products (one reformulated for the test and one commercially available) each were comprised of 9.8% fipronil and 8.8% S-methoprene. The spot-on product comprising fipronil, S-methoprene, and cyphenothrin was comprised of 9.8% fipronil, 8.8% S-methoprene, and 5.0% cyphenothrin. Dose volumes given to the treated dogs conformed to conventional dosages (i.e. 0.67 mL to dogs weighing less than 23 lbs, 1.67 mL to dogs weighing between 23 lbs and 44.9 lbs, and 2.68 mL to dogs weighing between 45 lbs and 88.9 lbs). The fourth subgroups of dogs in each weight category (i.e., Group 2D, 3D, and 4D) were treated with the test substances at a volume dose rate of 0.67 mL/kg which provides the calculated minimum active ingredients' dose rates that would be applied to dogs at the upper limit in the group weighing from 89 to 132 lbs.

TABLE 7

Grouping and Treatment

| Group | Weight | Treatment |
|---|---|---|
| 1 | 4 lb-60 lb | None |
| 2A | 4 lb-22.9 lb | Reformulated fipronil/S-methoprene |
| 2B | 23 lb-44.9 lb | Reformulated fipronil/S-methoprene |
| 2C | 45 lb-88.9 lb | Reformulated fipronil/S-methoprene |
| 2D | 25 lb-35.9 lb | Reformulated fipronil/S-methoprene |
| 3A | 4 lb-22.9 lb | fipronil/S-methoprene/cyphenothrin |
| 3B | 23 lb-44.9 lb | fipronil/S-methoprene/cyphenothrin |
| 3C | 45 lb-88.9 lb | fipronil/S-methoprene/cyphenothrin |
| 3D | 25 lb-35.9 lb | fipronil/S-methoprene/cyphenothrin |
| 4A | 4 lb-22.9 lb | Retail fipronil/S-methoprene |
| 4B | 23 lb-44.9 lb | Retail fipronil/S-methoprene |
| 4C | 45 lb-88.9 lb | Retail fipronil/S-methoprene |
| 4D | 25 lb-35.9 lb | Retail fipronil/S-methoprene |

The three active treatments were applied to the respective groups once at the beginning of the study (Day 0). The dogs were infested with fleas (*Ctenophalides felis*) and ticks (*Rhipicephalus sanguineus, Dermacentor variabilis*, and *Haemaphysalis elliptica*) in five intervals (Day −1, 7, 14, 21, and 28) for a period of approximately 4 weeks, with monitoring through Day 30 after treatment. For each subsequent infestation, the dogs of each treatment group were monitored to determine the kill rates for ticks at one hour after infestation, four hours after infestation, one day (24 hours) after infestation, and two days (48 hours) after infestation. Ticks were found by direct observation following parting of the hair coat and palpation in each area of the animal being examined (i.e. outside hind legs including feet, tail and anal areas, lateral area not including shoulders, abdominal area from chest to inside hind legs, fore legs and shoulders including feet, all neck and head areas, and dorsal strip from shoulder blades to base of tail). The efficacies (%) of the respective treatments on ticks at 24 and 48 hours after treatment/re-infestation and at 1 and 4 hours after treatment/re-infestation are shown in Tables 8 and 9.

Flea counts were made only at 48 hours after treatment (i.e., Day 2) and after each re-infestation (i.e., Days 9, 16, 23, and 30). A fine-toothed comb was used to recover fleas present in the animal's fur. The method of combing was by several strokes of the comb in each area of the animal being examined (i.e., outside hind legs including feet, tail and anal areas, lateral area not including shoulders, abdominal area from chest to inside hind legs, fore legs and shoulders including feet, all neck and head areas, and dorsal strip from shoulder blades to base of tail). Each stroke of the comb was made in the same direction following the pattern of the hair coat. Movement from one part of the animal's fur to the next was via strokes overlapping each other so that no area of fur was missed. The efficacies of the treatments on fleas are shown in Table 10.

TABLE 8

Treatment with Fipronil/Cyphenothrin Composition and Group Mean Efficacy
Against Ticks at 24 & 48 Hours After Treatment/Re-infestation

| Day | Time (hrs) | 2A | 2B | 2C | 2D | 3A | 3B | 3C | 3D | 4A | 4B | 4C | 4D |
|---|---|---|---|---|---|---|---|---|---|---|---|---|---|
| 0 (DV) | 24 | 61% | 78% | 96% | 0% | 30% | 74% | 91% | 39% | 74% | 52% | 78% | 70% |
|  | 48 | 76% | 82% | 100% | 76% | 80% | 94% | 100% | 82% | 88% | 94% | 94% | 94% |
| 0 (RS) | 24 | 73% | 68% | 74% | 56% | 83% | 57% | 92% | 71% | 61% | 61% | 86% | 73% |
|  | 48 | 73% | 79% | 97% | 67% | 90% | 81% | 100% | 84% | 94% | 67% | 90% | 97% |
| 7 (DV) | 24 | 94% | 96% | 97% | 97% | 100% | 99% | 100% | 98% | 98% | 98% | 97% | 89% |
|  | 48 | 98% | 100% | 100% | 100% | 100% | 100% | 100% | 99% | 100% | 100% | 100% | 100% |
| 7 (RS) | 24 | 96% | 96% | 97% | 95% | 100% | 100% | 100% | 95% | 100% | 92% | 92% | 92% |
|  | 48 | 99% | 100% | 100% | 100% | 100% | 100% | 100% | 100% | 100% | 100% | 95% | 95% |
| 14 (HE) | 24 | 91% | 97% | 97% | 85% | 49% | 100% | 77% | 86% | 91% | 88% | 81% | 76% |
|  | 48 | 94% | 100% | 98% | 91% | 80% | 98% | 100% | 95% | 98% | 98% | 94% | 90% |
| 21 (DV) | 24 | 92% | 90% | 96% | 72% | 69% | 86% | 92% | 92% | 55% | 56% | 93% | 49% |
|  | 48 | 100% | 100% | 100% | 97% | 98% | 100% | 100% | 95% | 95% | 86% | 100% | 80% |
| 21 (RS) | 24 | 95% | 87% | 97% | 80% | 99% | 99% | 99% | 85% | 79% | 83% | 85% | 66% |
|  | 48 | 99% | 98% | 98% | 86% | 100% | 99% | 100% | 95% | 97% | 90% | 99% | 79% |
| 28 (DV) | 24 | 70% | 94% | 72% | 36% | 75% | 18% | 87% | 70% | 34% | 15% | 18% | 1% |
|  | 48 | 99% | 99% | 100% | 65% | 93% | 68% | 99% | 90% | 92% | 64% | 93% | 71% |
| 28 (RS) | 24 | 59% | 90% | 97% | 66% | 89% | 84% | 94% | 56% | 31% | 54% | 70% | 31% |
|  | 48 | 96% | 99% | 98% | 90% | 95% | 94% | 98% | 94% | 93% | 85% | 94% | 69% |

DV = infested with *D. variabilis*;
RS = infested with *R. sanguineus*;
HE = infested with *H. elliptica*

As illustrated in Table 8, efficacy against existing ticks (Day −1 infestation) was irregular for all test substances at 24 and 48 hours after initial treatment. Overall, greater average tick kill rates for the treatment enhanced with cyphenothrin (Groups 3A, 3B, 3C, and 3D) were observed in all dog weight classes against both species of ticks recorded 24 hours following infestations. The effectiveness of the fipronil treatment enhanced with cyphenothrin against ticks 48 hours after treatment was >90% or just marginally below 90% for the different dog weight classes treated according to dose ranges. Table 8 also illustrates that treatment with a combination of fipronil/IGR and cyphenothrin provides prolonged efficacy for the treatment and prevention of tick infestation up to thirty days following application of the composition.

TABLE 9

Treatment with Fipronil/Cyphenothrin Composition and Group Mean
Immediate Efficacy Against Ticks at 1 & 4 Hours After Treatment/Re-infestation

| Treatment Day | Time (hrs) | 2A | 2B | 2C | 2D | 3A | 3B | 3C | 3D | 4A | 4B | 4C | 4D |
|---|---|---|---|---|---|---|---|---|---|---|---|---|---|
| 0 (DV) | 1 | 0% | 0% | 14% | 0% | 0% | 0% | 0% | 0% | 0% | 0% | 25% | 0% |
|  | 4 | 0% | 17% | 39% | 0% | 0% | 0% | 33% | 0% | 0% | 0% | 56% | 0% |
| 0 (RS) | 1 | 8% | 29% | 0% | 0% | 16% | 0% | 21% | 0% | 0% | 0% | 14% | 12% |
|  | 4 | 51% | 53% | 34% | 33% | 53% | 40% | 53% | 38% | 35% | 36% | 53% | 66% |
| 7 (DV) | 1 | 34% | 50% | 47% | 50% | 63% | 73% | 85% | 63% | 0% | 45% | 46% | 23% |
|  | 4 | 53% | 62% | 60% | 51% | 86% | 82% | 85% | 59% | 50% | 32% | 65% | 39% |
| 7 (RS) | 1 | 28% | 57% | 48% | 30% | 60% | 78% | 83% | 66% | 50% | 59% | 41% | 42% |
|  | 4 | 75% | 79% | 92% | 74% | 86% | 94% | 92% | 77% | 81% | 77% | 80% | 60% |
| 14 (HE) | 1 | 31% | 0% | 0% | 19% | 0% | 8% | 21% | 0% | 0% | 24% | 57% | 19% |
|  | 4 | 31% | 20% | 51% | 14% | 0% | 28% | 17% | 0% | 7% | 23% | 40% | 23% |
| 21 (DV) | 1 | 2% | 16% | 21% | 0% | 43% | 15% | 48% | 36% | 0% | 2% | 2% | 0% |
|  | 4 | 17% | 26% | 25% | 0% | 33% | 26% | 47% | 38% | 0% | 0% | 44% | 0% |
| 21 (RS) | 1 | 0% | 15% | 18% | 28% | 55% | 64% | 74% | 73% | 14% | 19% | 36% | 0% |
|  | 4 | 45% | 28% | 67% | 46% | 63% | 86% | 94% | 60% | 39% | 39% | 40% | 9% |
| 28 (DV) | 1 | 0% | 0% | 0% | 0% | 0% | 0% | 0% | 29% | 0% | 0% | 0% | 0% |
|  | 4 | 0% | 0% | 24% | 0% | 0% | 0% | 0% | 31% | 0% | 0% | 1% | 0% |
| 28 (RS) | 1 | 8% | 38% | 0% | 40% | 8% | 22% | 62% | 32% | 0% | 4% | 0% | 22% |
|  | 4 | 37% | 40% | 39% | 64% | 61% | 63% | 67% | 41% | 12% | 24% | 13% | 24% |

DV = infested with *D. variabilis*;
RS = infested with *R. sanguineus*;
HE = infested with *H. elliptica*

Table 9 illustrates that the enhanced spot-on composition consistently provided better immediate efficacy against new ticks, especially when compared to the compositions lacking cyphenothrin (Groups 2 and 4). Efficacy in killing/repelling ticks at 1 and 4 hours after re-infestation was observed for both species of ticks on Days 7 and 21 and for *R. sanguineus* on Day 28. Thus, Table 9 illustrates that treatment with a combination of fipronil and cyphenothrin results in significantly greater average kill rates and speed of kill for ticks at one hour and four hours after an initial treatment and after subsequent re-infestations.

TABLE 10

Treatment with Fipronil/Cyphenothrin Composition and Group Mean Efficacy Against Fleas at 48 Hours after Treatment/Re-infestation

| Treatment Day | 2A | 2B | 2C | 2D | 3A | 3B | 3C | 3D | 4A | 4B | 4C | 4D |
|---|---|---|---|---|---|---|---|---|---|---|---|---|
| 2  | 100% | 100% | 100% | 100% | 100% | 100% | 100% | 100% | 100% | 100% | 100% | 99% |
| 9  | 100% | 100% | 100% | 100% | 100% | 100% | 100% | 100% | 100% | 100% | 100% | 100% |
| 16 | 100% | 100% | 100% | 100% | 100% | 100% | 100% | 100% | 100% | 100% | 100% | 100% |
| 23 | 100% | 100% | 100% | 100% | 100% | 100% | 100% | 100% | 100% | 100% | 100% | 100% |
| 30 | 100% | 100% | 100% | 100% | 100% | 100% | 100% | 100% | 100% | 97%  | 100% | 98% |

Table 10 illustrates that the efficacy of the composition enhanced with cyphenothrin was at 100% for all dog weights throughout the study (i.e. up to Day 30), whereas the efficacy of the retail fipronil/IGR composition failed to remain at 100% efficacy for mid-weight range dogs.

In summary, efficacy of the enhanced formulation against fleas, measured at 48 hours after treatment and after re-infestation was 100%. The cyphenothrin-enhanced formulation was often more efficacious compared to the commercially marketed fipronil/IGR formulation not containing cyphenothrin. Residual efficacy against new tick infestations over the 30 days after treatment was well above 90% in all of the weight groups, but was much less than 90% in half of the weight groups for the commercial product in the final week of the study. Enhancement of the formulation with 5% cyphenothrin improved immediate efficacy against new ticks (*D. variabilis* and *R. sanguineus*) on the $7^{th}$ and $21^{st}$ days and for *R. sanguineus* on the $28^{th}$ day. Comparing the enhanced formulation with the two fipronil-only test substances showed that the enhanced test substance provided statistically greater repellent action at 1 and 4 hours after re-infestation.

EXAMPLE 7

Efficacy Evaluation of a Spot-on Composition Containing Fipronil/S-Methoprene Compared to a Spot-on Composition Containing Fipronil/S-Methoprene/Etofenprox for the Treatment of Fleas and Ticks on Cats A double blind, randomized, single-centered, controlled study was performed to illustrate the efficacy of a fipronil/IGR spot-on composition enhanced with etofenprox compared to fipronil/IGR spot-on compositions not enhanced with etofenprox in the treatment of ticks and fleas on cats. An experimental spot-on formulation comprising 9.8% fipronil and 11.8% S-methoprene was enhanced by adding 15% etofenprox. This enhanced composition, along with two fipronil/S-methoprene formulations not enhanced with etofenprox, were evaluated for efficacy against pre-existing fleas and ticks.

The study was conducted on seven groups of cats, each group consisting of six cats for a total of 42 cats. The cats were randomly allocated to the seven groups. Etofenprox technical active (97% a.i.) was added at the rate of 15% to a basic fipronil-methoprene formulation (9.8% fipronil, 11.8% S-methoprene) to provide an enhanced formulation. The two fipronil-methoprene formulations not containing etofenprox were comprised of 9.8% and 11.8% S-methoprene. One fipronil/methoprene formulation was reformulated for the test and one was commercially available, which served as the positive control for the study. The enhanced formulation was applied at a 0.50 mL unit dose to a group of six treated cats (Group 2A). The unenhanced formulations were applied at a 0.50 mL unit dose to two groups each of six cats (Groups 3A and 4A). Three additional groups, each of six cats, were treated by applying the test substances at the minimum dose rate, equivalent to treating cats weighing 20 lb with dose volumes of 0.5 mL (approximately 0.055 mL/kg). The enhanced formulation was administered at this dosage to Group 2B and the unenhanced formulations were administered at this dosage to Groups 3B and 4B. The weight specifications for all treated cats were 10 lb+/−5 lb. A seventh group of six cats (Group 1) served as untreated controls. Table 11 sets forth the grouping, treatment and dosage of the cats in the study.

TABLE 11

Grouping, Treatment, and Dosage

| Group | Weight | Dosage | Treatment |
|---|---|---|---|
| 1  | 5 lb-15 lb | None | None |
| 2A | 5 lb-15 lb | 0.5 mL/cat | fipronil/S-methoprene/etofenprox |
| 2B | 5 lb-15 lb | 0.055 mL/kg | fipronil/S-methoprene/etofenprox |
| 3A | 5 lb-15 lb | 0.5 mL/cat | Reformulated fipronil/S-methoprene |
| 3B | 5 lb-15 lb | 0.055 mL/kg | Reformulated fipronil/S-methoprene |
| 4A | 5 lb-15 lb | 0.5 mL/cat | Retail fipronil/S-methoprene |
| 4B | 5 lb-15 lb | 0.055 mL/kg | Retail fipronil/S-methoprene |

The cats were infested with 100 fleas (*Ctenophalides felis*) on Days −1, 7, 14, 21, and 28 and 50 ticks (*Rhipicephalus turanicus* on Day 7, *Dermacentor variabilis* on Days −1, 21, and 28), and *Haemaphysalis elliptica* on Day 14) for a period of approximately 4 weeks, with monitoring through Day 30 after treatment. Tick counts, without disturbing or removing ticks, were conducted at one hour and four hours after application of the test substances on the day of treatment (Day 0) and similarly after re-infestation on Days 8, 15, 22, and 28, in order to determine the speed of kill as evidence of repellency. Tick counts were also made at 24 and 48 hours after treatment and after each re-infestation. Ticks were found by direct observation following parting of the hair coat and palpation in each area of the animal being examined (i.e. outside hind legs including feet, tail and anal areas, lateral area not including shoulders, abdominal area from chest to inside hind legs, fore legs and shoulders including feet, all neck and head areas, and dorsal strip from shoulder blades to base of tail). The efficacies (%) of the respective treatments on ticks at 24 hours and 48 hours after treatment and after re-infestation are shown in Table 12. The efficacies (%) of the respective treatments on ticks at 1 hour and 4 hours after treatment and after re-infestation are shown in Table 13.

TABLE 12

Group Mean Efficacy Against Ticks at 24 & 48 Hours After Treatment/Re-infestation

| Treatment | Time | Group | | | | | |
|---|---|---|---|---|---|---|---|
| Day | (hrs) | 2A | 2B | 3A | 3B | 4A | 4B |
| 0 (DV) | 24 | 75% | 77% | 94% | 50% | 87% | 65% |
|  | 48 | 100% | 86% | 100% | 58% | 100% | 51% |
| 7 (RT) | 24 | 98% | 77% | 100% | 87% | 100% | 55% |
|  | 48 | 100% | 98% | 100% | 100% | 98% | 100% |
| 14 (HE) | 24 | 62% | 77% | 90%* | 58% | 73% | 55% |
|  | 48 | 99% | 88% | 99% | 89% | 99% | 89% |
| 21 (DV) | 24 | 91% | 77% | 92% | 97% | 91% | 84% |
|  | 48 | 99% | 89% | 99% | 98% | 92% | 91% |
| 28 (DV) | 24 | 90% | 85% | 90%* | 68% | 91% | 36% |
|  | 48 | 98% | 91% | 99% | 72% | 94% | 46% |

Bold type indicates meets/exceeds 90% (unless rounding increases to 90% *)

As shown in Table 12, all three test substances at full label dose (0.5 mL) performed similarly by attaining/exceeding 90% efficacy for killing/repelling ticks at 48 hours after treatment and re-infestation. Occasionally, adequate efficacy (=/>90%) against ticks was shown also at 24 hours after treatment or after re-infestation, almost exclusively for the groups that receive the full label dose rate. Groups treated at the minimum dose rate (Groups 2B, 3B, and 4B) attained 90% efficacy or marginally below 90% efficacy (i.e. at least between 85%-89%) against fleas at 48 hours, except for the positive control group (Group 4B) in the fourth week.

TABLE 13

Group Mean Efficacy Against Ticks at 1 and 4 Hours After Treatment/Re-infestation

| Treatment | Time | Group | | | | | |
|---|---|---|---|---|---|---|---|
| Day | (hrs) | 2A | 2B | 3A | 3B | 4A | 4B |
| 0 (DV) | 1 | 0% | 2% | 52% | 7% | 21% | 24% |
|  | 4 | 15% | 12% | 51% | 57% | 34% | 49% |
| 7 (RT) | 1 | 46% | 2% | 30% | 14% | 0% | 0% |
|  | 4 | 59% | 12% | 35% | 29% | 0% | 6% |
| 14 (HE) | 1 | 0% | 27% | 0% | 0% | 0% | 0% |
|  | 4 | 0% | 63% | 5% | 4% | 0% | 0% |
| 21 (DV) | 1 | 56% | 27% | 69% | 72% | 50% | 35% |
|  | 4 | 91% | 63% | 89% | 98% | 85% | 86% |
| 28 (DV) | 1 | 57% | 47% | 47% | 0% | 65% | 0% |
|  | 4 | 89% | 86% | 81% | 66% | 92% | 37% |

DV = infested with *D. variabilis*;
RT = infested with *R. turanicus*;
HE = infested with *H. elliptica*;
Bold type indicates meets/exceeds 90%

Table 13 illustrates that efficacy in killing/repelling ticks at 1 hour and 4 hours after treatment and after re-infestation did not show improvement in immediate efficacy attributable to the etofenprox enhancement of the basic fipronil-methoprene formulation. On only three occasions (at 4 hour counts) was adequate (=/>90%) immediate efficacy shown against ticks and these three events did not appear to be consistently related to formulation or to dose rate.

TABLE 14

Group Mean Efficacy Against Fleas at 48 Hours After Treatment/Re-infestation

| Treatment | Group | | | | | |
|---|---|---|---|---|---|---|
| Day | 2A | 2B | 3A | 3B | 4A | 4B |
| 2 | 99% | 100% | 100% | 99% | 99% | 98% |
| 9 | 100% | 100% | 100% | 100% | 100% | 100% |
| 16 | 100% | 100% | 100% | 100% | 100% | 100% |
| 23 | 100% | 100% | 100% | 100% | 100% | 98% |
| 30 | 97% | 93% | 100% | 99% | 100% | 85% |

Bold type indicates meets/exceeds 90%

Table 14 illustrates that the three treatments administered to cats at a minimal dose of 0.055 mL/kg all had a greater than 90% immediate efficacies against fleas and persistent efficacies >90% for four weeks (Groups 2B and 3B) and three weeks (Group 4B). Table 10 further shows that the three treatments administered to cats at a dose of 0.50 mL/cat all had immediate (Day 2) and four week persistent efficacies of >90% against fleas.

In summary, the only test substance that provided 90% or better efficacy against fleas and ticks at both full and minimum dose rate at the end of the study was the enhanced fipronil-methoprene (Group 2) and the positive control test substances (Group 4), when administered at full label dose rate only (Groups 2A and 4A). Both also provided adequate efficacy against fleas and ticks in the fourth week of the study.

EXAMPLE 8

Testing of a Fipronil and S-Methoprene Composition Against the Enhanced Spot-on Composition Comprising Fipronil, S-Methoprene, and Cyphenothrin A double blind, controlled study was performed to illustrate the difference in kill rates for ticks and fleas between treatment with a spot-on composition containing fipronil and S-methoprene and treatment with an enhanced spot-on composition comprising fipronil, S-methoprene, and cyphenothrin prepared in a similar manner to Example 2.

A total of 18 dogs were randomized into three treatment groups. Group A was the control group and did not receive treatment. Group B comprised an active treatment group that received treatment with the enhanced combination of 9.8% fipronil, 8.8% S-methoprene, and 5% cyphenothrin. Group C comprised an active treatment group that received treatment with the combination of 9.8% fipronil and 8.8% S-methoprene. For all treatments, a spot-on application was developed and applied to the dogs in a manner in accordance with this invention. All dogs admitted into the experiment were first deemed to be suffering from both flea and tick infestation. The experiment was designed such that all treatment groups were administered the appropriate treatment and then observed one hour and four hours after application. During the post-application observation periods, the dogs were contacted with a piece of test paper in defined areas of the dog's body, for a defined period of time. The paper was designed such that dead ticks and fleas would adhere to the paper, and the number of dead ticks and fleas could be counted for comparison to the control group (Group A) to determine the reduction in pests due to treatment. In addition, the number of ticks and fleas remaining on the dog within the observation area was also calculated. The results of the experiment are shown in Table 15.

TABLE 15

Kill Data for Treatment of Ticks and Fleas

| | | | | +1 Hour | | | | +4 Hours | | | | | |
| --- | --- | --- | --- | --- | --- | --- | --- | --- | --- | --- | --- | --- | --- |
| | | | | On Dog | | Dead On Paper | | On Dog | | Dead On Paper | | Total Dead on Paper | |
| Run # | Cage | Dog # | Group | Ticks | Fleas | Ticks | Fleas | Ticks | Fleas | Ticks | Fleas | Ticks | Fleas |
| 30 | 110 | 468 | A | 19 | 26 | 0 | 1 | 18 | 20 | 0 | 0 | 0 | 1 |
| 32 | 112 | 411 | A | 34 | 38 | 0 | 0 | 25 | 34 | 0 | 0 | 0 | 0 |
| 34 | 114 | 357 | A | 32 | 56 | 0 | 1 | 36 | 52 | 0 | 2 | 0 | 3 |
| 36 | 116 | 356 | A | 21 | 28 | 0 | 0 | 22 | 23 | 0 | 0 | 0 | 0 |
| 38 | 118 | 457 | A | 31 | 39 | 0 | 1 | 30 | 35 | 0 | 1 | 0 | 2 |
| 40 | 120 | 424 | A | 41 | 33 | 0 | 0 | 35 | 30 | 0 | 2 | 0 | 2 |
| | | Average | | 29.7 | 36.7 | 0.0 | 0.5 | 27.7 | 32.3 | 0.0 | 0.8 | 0.0 | 1.3 |
| 44 | IS1 | 471 | B | 9 | 8 | 18 | 25 | 6 | 1 | 10 | 18 | 28 | 43 |
| 46 | IS2 | 430 | B | 0 | 3 | 48 | 59 | 0 | 0 | 1 | 6 | 49 | 65 |
| 48 | 11 | 229 | B | 1 | 0 | 49 | 42 | 0 | 0 | 3 | 12 | 52 | 54 |
| 50 | 50 | 301 | B | 6 | 13 | 36 | 36 | 0 | 6 | 7 | 24 | 43 | 60 |
| 52 | 52 | 429 | B | 2 | 10 | 46 | 58 | 0 | 1 | 2 | 14 | 48 | 72 |
| 54 | 54 | 412 | B | 4 | 20 | 43 | 39 | 0 | 0 | 4 | 24 | 47 | 63 |
| | | Average | | 3.7 | 9.0 | 40.0 | 43.2 | 1.0 | 1.3 | 4.5 | 16.3 | 44.5 | 59.5 |
| | | % Reduction | | 87.6% | 75.5% | | | 96.4% | 95.9% | | | | |
| 58 | 58 | 420 | C | 24 | 18 | 8 | 6 | 0 | 5 | 20 | 32 | 28 | 38 |
| 60 | 60 | 470 | C | 34 | 47 | 4 | 13 | 1 | 10 | 18 | 34 | 22 | 47 |
| 62 | 62 | 222 | C | 25 | 34 | 7 | 14 | 1 | 5 | 25 | 33 | 32 | 47 |
| 64 | 64 | 449 | C | 28 | 40 | 3 | 4 | 3 | 21 | 27 | 35 | 30 | 39 |
| 66 | 66 | 464 | C | 27 | 33 | 7 | 5 | 2 | 2 | 30 | 53 | 37 | 58 |
| 68 | 68 | 463 | C | 25 | 21 | 4 | 6 | 2 | 3 | 25 | 47 | 29 | 53 |
| | | Average | | 27.2 | 32.2 | 5.5 | 8.0 | 1.5 | 7.7 | 24.2 | 39.0 | 29.7 | 47.0 |
| | | % Reduction | | 8.4% | 12.3% | | | 94.6% | 76.3% | | | | |

As is evident from Table 15, Group B (treatment including cyphenothrin) experienced a greater decrease in the number of ticks and fleas killed within the first hour of treatment compared to Group C (treatment without cyphenothrin). Using Group A as an average baseline for the number of ticks and fleas present on an infested dog, the dogs in Group B experienced a 87.6% and 75.5% decrease in the average number of ticks and fleas present on the dog's skin, respectively, after one hour. Alternatively, the dogs in Group C only experienced an 8.4% and 12.3% decrease in the average number of ticks and fleas present on the dog's skin, respectively, after one hour.

Furthermore, at the four-hour interval, dogs in Group B experienced an average reduction in the number of ticks and fleas remaining on the skin of the animal of 96.4% and 95.9%, respectively. The dogs in Group C experienced an average reduction of 94.6% and 76.3%. Thus, the average reduction in ticks on the animals was similar, but the average reduction in fleas on the dog's skin was significantly higher (95.9% in Group B vs. 76.3% in Group C). Finally, the total number of dead ticks and fleas dead on the paper was higher for Group B, compared to Group C. Treatment Group B experienced a total kill rate, on average, of 44.5 ticks and 59.5 fleas over the course of the four-hour interval, compared to a total average kill rate of 29.7 ticks and 49.0 fleas for treatment Group C. As such, treatment with a combination of fipronil, S-methoprene, and cyphenothrin resulted in a significantly higher average kill rate after one hour, and maintained a greater average kill rate for both ticks and fleas, four hours after treatment.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A spot-on pesticidal composition comprising about 1% to about 20% (w/w) fipronil, about 1% to 15% (w/w) cyphenothrin, about 1% to about 20% (w/w) insect growth regulator, and about 55% to about 85% (w/w) organic solvent, wherein the organic solvent has a dielectric constant ranging from about 1 to 40, a boiling point less than 100° C., and a density less than the density of water.

2. The spot-on pesticidal composition of claim 1, wherein the insect growth regulator is selected from the group consisting of bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, triflumuron, epofenonane, fenoxycarb, hydroprene, kinoprene, S-methoprene, pyriproxyfen, triprene, and combinations thereof.

3. The spot-on pesticidal composition of claim 1, comprising about 5% to about 15% (w/w) fipronil, about 2% to about 10% (w/w) cyphenothrin, and about 2% to about 15% (w/w) insect growth regulator.

4. The spot-on pesticidal composition of claim 1, comprising about 8% to about 10% (w/w) fipronil, about 4% to about 6% (w/w) cyphenothrin, and about 7% to about 10% (w/w) insect growth regulator.

5. The spot-on pesticidal composition of claim 4, wherein the insect growth regulator is S-methoprene.

6. The spot-on pesticidal composition of claim 1, comprising about 8% to about 10% (w/w) fipronil, about 4% to about 6% (w/w) cyphenothrin, and about 3% to about 5% (w/w) insect growth regulator.

7. The spot-on pesticidal composition of claim 6, wherein the insect growth regulator is pyriproxyfen.

8. The spot-on pesticidal composition of claim 1, wherein the organic solvent is selected from the group consisting of acetyltributyl citrate, fatty acid esters, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, diethylene glycol monoethyl ether, monomethylacetamide, dipropylene glycol monomethyl ether, liquid polyoxyethylene glycols, propylene glycol, 2-pyrrolidones, ethylene glycol, diethyl phthalate, ethoxydiglycol, and combinations thereof.

9. The spot-on pesticidal composition of claim 1, wherein the organic solvent is diethylene glycol monoethyl ether.

10. The spot-on pesticidal composition of claim 1, wherein the composition further comprises an antioxidant.

11. The spot-on pesticidal composition of claim 10, wherein the antioxidant is present in the composition at a concentration of about 1% to about 10% (w/w).

12. The spot-on pesticidal composition of claim 10, wherein the antioxidant is a vitamin E compound.

13. The spot-on pesticidal composition of claim 10, wherein the antioxidant is selected from the group consisting of tocopherol acetate, tocopherol linoleate, tocopherol nicotinate, tocopherol succinate, ascorbyl tocopherol phosphate, dioleyl tocopherol methylsilanol, tocophersolan, tocopherol linoleate/oleate, and combinations thereof.

14. The spot-on pesticidal composition of claim 1, wherein the composition provides at least 90% efficacy against insect and pest pupae for a period of at least 30 days following administration of the composition to a mammal.

15. The spot-on pesticidal composition of claim 14, wherein the mammal comprises a dog or cat.

16. A spot-on pesticidal composition, comprising:
a. 8% to 11% (w/w) fipronil;
b. 4% to 6% (w/w) cyphenothrin;
c. 8% to 12% (w/w) S-methoprene;
d. 65% to 70% (w/w) organic solvent; and
e. 4% to 6% (w/w) antioxidant.

17. A spot-on pesticidal composition, comprising:
a. 8% to 11% (w/w) fipronil;
b. 7% to 9% (w/w) cyphenothrin;
c. 8% to 12% (w/w) S-methoprene;
d. 65% to 70% (w/w) organic solvent; and
e. 4% to 6% (w/w) antioxidant.

18. A spot-on pesticidal composition, comprising:
a. 8% to 11% (w/w) fipronil;
b. 4% to 6% (w/w) cyphenothrin;
c. 3% to 5% (w/w) pyriproxyfen;
d. 75% to 80% (w/w) organic solvent; and
e. 4% to 6% (w/w) antioxidant.

19. A spot-on pesticidal composition, comprising:
a. 8% to 11% (w/w) fipronil;
b. 7% to 9% (w/w) cyphenothrin;
c. 3% to 5% (w/w) pyriproxyfen;
d. 75% to 80% (w/w) organic solvent; and
e. 4% to 6% (w/w) antioxidant.

20. A spot-on pesticidal composition, comprising about 5% to about 15% (w/w) fipronil, about 2% to about 10% (w/w) cyphenothrin, and about 1% to about 20% (w/w) insect growth regulator.

21. A spot-on pesticidal composition, comprising:
a. 9% to 11% (w/w) fipronil;
b. 5% to 9% (w/w) cyphenothrin;
c. 3% to 5% (w/w) pyriproxyfen; and
c. 75% to 80% (w/w) diethylene glycol monoethyl ether.

22. A method of killing insect and pest pupae and adults on an animal, which method comprises administering a localized cutaneous application between the shoulders of the animal, a spot-on composition comprising about 1% to about 20% (w/w) fipronil, about 1% to 15% (w/w) cyphenothrin, about 1% to about 20% (w/w) insect growth regulator, and about 55% to about 85% (w/w) organic solvent, wherein the composition is administered in a volume sufficient to deliver a dosage of fipronil, cyphenothrin, and insect growth regulator ranging from about 0.1 mg/kg to about 40 mg/kg of animal weight, and wherein at least 90% efficacy against insect and pest pupae is achieved.

23. The method of claim 22, wherein the application is made as a one-time treatment.

24. The method of claim 22, wherein the application is made every six weeks.

25. The method of claim 22, wherein the application is made every five weeks.

26. The method of claim 22, wherein the application is made every four weeks.

27. The method of claim 22, wherein the application is made every week.

28. The method of claim 22, wherein the animal is a mammal.

29. The method of claim 28, wherein the mammal comprises a dog or a cat.

30. The method of claim 22, wherein the spot-on composition additionally comprises about 1% to about 10% (w/w) of an antioxidant.

31. The method of claim 22, wherein at least 95% efficacy is achieved.

* * * * *